(12) United States Patent
Kwak et al.

(10) Patent No.: US 12,026,878 B2
(45) Date of Patent: Jul. 2, 2024

(54) LEARNING METHOD FOR GENERATING MULTIPHASE COLLATERAL IMAGE AND MULTIPHASE COLLATERAL IMAGE GENERATING METHOD USING MACHING LEARNING

(71) Applicants: THE CATHOLIC UNIVERSITY OF KOREA INDUSTRY-ACADEMIC COOPERATION FOUNDATION, Seoul (KR); KONKUK UNIVERSITY GLOCAL INDUSTRY-ACADEMIC COLLABORATION FOUNDATION, Chungju-si (KR)

(72) Inventors: Jin Tae Kwak, Seoul (KR); Nhat To Minh Nguyen, Seoul (KR); Hyun Jeong Kim, Daejeon (KR); Hong Gee Roh, Seoul (KR)

(73) Assignees: THE CATHOLIC UNIVERSITY OF KOREA INDUSTRY-ACADEMIC COOPERATION FOUNDATION, Seoul (KR); KONKUK UNIVERSITY GLOCAL INDUSTRY-ACADEMIC COLLABORATION FOUNDATION, Chungju-si (KR)

( * ) Notice: Subject to any disclaimer, the term of this patent is extended or adjusted under 35 U.S.C. 154(b) by 372 days.

(21) Appl. No.: 17/483,711

(22) Filed: Sep. 23, 2021

(65) Prior Publication Data
US 2022/0012883 A1 Jan. 13, 2022

Related U.S. Application Data

(63) Continuation of application No. PCT/KR2020/003981, filed on Mar. 24, 2020.

(30) Foreign Application Priority Data

Mar. 25, 2019 (KR) .......................... 10-2019-0033332

(51) Int. Cl.
*G06T 7/00* (2017.01)
*A61B 6/50* (2024.01)

(52) U.S. Cl.
CPC ............ *G06T 7/0012* (2013.01); *A61B 6/501* (2013.01); *G06T 2207/10088* (2013.01); *G06T 2207/20081* (2013.01); *G06T 2207/30016* (2013.01)

(58) Field of Classification Search
CPC ......... G06V 2201/03–034; G06T 2207/10088; G06T 7/10–194; A61B 6/501
See application file for complete search history.

(56) References Cited

U.S. PATENT DOCUMENTS 10,420,610 B2 * 9/2019 Bai .................... A61B 6/504
11,647,915 B2 * 5/2023 Fielden ............... A61B 5/055
600/419

(Continued)

FOREIGN PATENT DOCUMENTS

KR 10-2015-0128471 A 11/2015
KR 10-1754291 B1 7/2017

(Continued)

OTHER PUBLICATIONS

International Search Report and Written Opinion of International application No. PCT /KR2020/003981. Sep. 11, 2020.

(Continued)

*Primary Examiner* — Sean T Motsinger

(57) ABSTRACT

A learning method for generating a multiphase collateral image comprises the steps of: receiving inputs of an MRI image of a head part and a multiphase collateral image generated on the basis of the MRI image; generating a brain mask by using the MRI image; generating an MRI image and a multiphase collateral image which are masked by the brain mask; and learning the masked multiphase collateral (Continued)

image for the masked MRI image by using a learning network.

8 Claims, 6 Drawing Sheets

(56) References Cited

U.S. PATENT DOCUMENTS

| | | | | |
|---|---|---|---|---|
| 2004/0127799 | A1* | 7/2004 | Sorensen | G06T 7/0012 |
| | | | | 600/481 |
| 2010/0067761 | A1 | 3/2010 | Jakobsson et al. | |
| 2010/0240983 | A1* | 9/2010 | Jung | G01R 33/56366 |
| | | | | 600/410 |
| 2018/0374213 | A1* | 12/2018 | Arnold | G06N 5/046 |
| 2019/0130609 | A1* | 5/2019 | Chappell | G06T 7/0012 |
| 2019/0150764 | A1* | 5/2019 | Arnold | G06V 10/82 |
| 2020/0020082 | A1* | 1/2020 | Zahneisen | G06T 7/0012 |
| 2020/0315455 | A1* | 10/2020 | Lee | A61B 5/4082 |
| 2021/0015438 | A1* | 1/2021 | Sahbaee Bagherzadeh | G16H 50/20 |
| 2021/0128092 | A1* | 5/2021 | Vaz | A61B 6/40 |
| 2021/0128095 | A1* | 5/2021 | Vaz | G06T 11/003 |
| 2021/0128818 | A1* | 5/2021 | Vaz | A61B 6/507 |
| 2021/0133960 | A1* | 5/2021 | Vaz | A61B 6/481 |
| 2021/0133961 | A1* | 5/2021 | Itu | G06N 20/00 |
| 2022/0125314 | A1* | 4/2022 | Meyer | G01R 33/4835 |
| 2023/0177746 | A1* | 6/2023 | Shao | G16H 50/20 |
| | | | | 382/131 |
| 2023/0260661 | A1* | 8/2023 | Yang | G06T 7/00 |
| | | | | 703/11 |

FOREIGN PATENT DOCUMENTS

| | | | | |
|---|---|---|---|---|
| KR | 10-1885998 | B1 | 8/2018 | |
| KR | 1885998 | B1 * | 8/2018 | A61B 5/0263 |
| KR | 10-2019-0028901 | A | 3/2019 | |
| WO | 2018/015414 | A1 | 1/2018 | |

OTHER PUBLICATIONS

Nguyen Ho Minh Duy et al: "Accurate brain extraction using Active Shape Model and Convolutional Neural Networks", arxiv.org, Cornell University Library, 201 Olin Library Cornell University Ithaca, NY 14853, Feb. 5, 2018, (Feb. 5, 2018), XP080857121.

* cited by examiner

LEARNING METHOD FOR GENERATING MULTIPHASE COLLATERAL IMAGE AND MULTIPHASE COLLATERAL IMAGE GENERATING METHOD USING MACHING LEARNING

CROSS-REFERENCE TO RELATED APPLICATIONS

This application is a continuation of pending PCT International Application No. PCT/KR2020/003981, which was filed on Mar. 24, 2020, and which claims priority from Korean Patent Application No. 10-2019-0033332 filed on Mar. 25, 2019. The disclosure of the above patent application is incorporated herein by reference in their entirety.

BACKGROUND

Technical Field

The present disclosure relates to a learning method for generating multiphase collateral images which may be used for diagnosing various cerebrovascular diseases such as stroke and making a prognosis and a method of generating multiphase collateral images using machine learning.

Background Art

Acute ischemic stroke is one of major diseases which threaten the life and health of numerous people all over the world, and it is important to quickly and accurately diagnose and treat the first onset. The technological development of interventional neuroradiology including endovascular thrombectomy greatly contributes to an improvement in death rate related to stroke, but a significant number of patients still die or do not recover normal functions.

A clinician should make the best decision by comprehensively considering various images and clinical information for the diagnosis and treatment of stroke. In particular, image information is very important and decisive in the diagnosis of a stroke. With the development of medical imaging equipment and image levels, the utilization of medical images is gradually increasing, and thus acquisition and reconstruction of medical images, the complexity of interpretation of an imaging examination and number of readings of medical images are continuously increasing. This is causing an increase in the workload imposed on clinicians and a decrease in the accuracy and efficiency of diagnosis.

Among several prognostic factors of stroke, collateral flow is a biological reaction mechanism for maintaining blood supply to ischemia tissue surrounding a cerebral infarct and was disclosed as an independent factor which has a crucial influence on proximal brain perfusion of occluded cerebrovascular. In conventional research related to collateral flow, multiphase computed tomography (CT) angiography and perfusion magnetic resonance imaging (MRI) are mainly used. According to multiphase CT angiography, it is not possible to accurately know an infarct range, and there is a disadvantage of radiation exposure. Also, according to a multiphase imaging method based on perfusion MRI images, it is not possible to know blood vessel information. Here, in the case of adding a blood vessel image, the amount of imaging time and the usage of a contrast medium increase.

In addition, conventional collateral flow measurement and evaluation generally involves multiphase image reconstruction based on an experiential technique and qualitative evaluation of reconstructed images. Therefore, the objectivity of the interpretation of the results may be degraded, and it is not possible to reflect a hemodynamic difference between individual patients.

DISCLOSURE

Technical Problem

The present disclosure is directed to providing a learning method for rapidly and accurately generating multiphase collateral images.

The present disclosure is directed to providing a method of generating multiphase collateral images using machine learning.

Technical Solution

An aspect of the present disclosure provides a learning method for generating multiphase collateral images, the learning method including receiving a magnetic resonance imaging (MRI) image of a head and multiphase collateral images generated on the basis of the MRI image, generating a brain mask using the MRI image, generating an MRI image and multiphase collateral images which are masked by the brain mask; and learning the masked multiphase collateral images for the masked MRI image using a learning network.

Another aspect of the present disclosure provides a method of generating multiphase collateral images using machine learning, the method including receiving an MRI image of a subject's head and generating multiphase collateral images for the MRI image using a learning network. The learning network is a network which has learned reference multiphase collateral images for reference MRI images.

Advantageous Effects

According to an embodiment of the present disclosure, multiphase collateral images are estimated through machine learning. Accordingly, it is possible to rapidly generate multiphase collateral images, and a diagnosis rate of cerebrovascular diseases, such as stroke, can also be increased.

Also, according to an embodiment of the present disclosure, multiphase collateral images are generated without subjective judgment which may vary depending on experts. Accordingly, generation of multiphase collateral images and diagnosis of a cerebrovascular disease can be objectively performed.

Further, according to an embodiment of the present disclosure, only MRI images of brains are learned using a brain mask, and thus a learning rate can be increased.

BRIEF DESCRIPTION OF DRAWINGS

FIG. 5A shows an MRI image, FIG. 5B shows a brain mask for the MRI image shown in FIG. 5A, and FIG. 5C shows a masked MRI image.

FIG. 7A is a diagram illustrating a process of generating a feature map through convolution, and FIG. 7B is a diagram illustrating a process of increasing a size of the feature map through deconvolution.

Modes of the Disclosure

Figure 1:
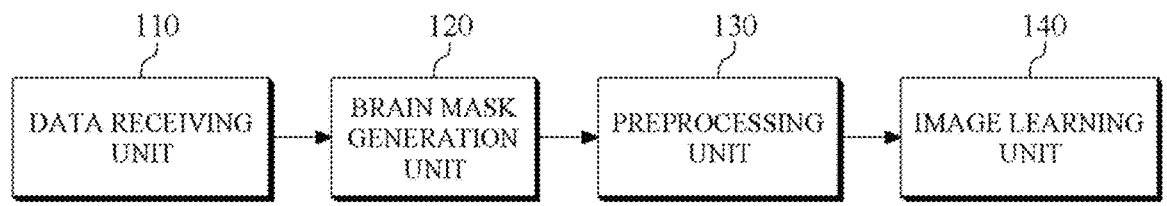
FIG. 1 is a block diagram of a learning device for generating multiphase collateral images according to an embodiment of the present disclosure.

Since the present disclosure may be variously modified and may include various embodiments, specific embodiments will be illustrated in the drawings and described in detail in the detailed description. However, it should be understood that they are not intended to limit the present disclosure to specific embodiments but rather to encompass all modifications, similarities, and alternatives which fall within the spirit and technical scope of the present disclosure. In describing each drawing, like reference numbers refer to like elements.

Multiphase collateral images refer to images of five blood flow phases, an artery phase, a capillary phase, early and late venous phases, and a delayed phase.

From multiphase collateral images of a brain, it is possible to diagnose a cerebrovascular disease, such as stroke, or predict a prognosis after surgery. Multiphase collateral images may be obtained by post-processing an image of a patient's head which is obtained through magnetic resonance imaging (MRI) equipment. The post-processing is generally performed by a clinical specialist manipulating the MRI image on the basis of his or her experience. In other words, the clinical specialist generates the multiphase collateral images from the already-generated MRI image by manually operating a computer.

Therefore, it takes a great deal of time to generate the multiphase collateral images, and objectivity in interpreting multiphase collateral images may be degraded. Particularly, in an urgent situation in which an acute cerebrovascular disease occurs, the time required for generating multiphase collateral images may be very fatal.

For this reason, the present disclosure proposes a method of generating multiphase collateral images using machine learning and a learning method for generating multiphase collateral images. According to an embodiment of the present disclosure, multiphase collateral images of a brain are estimated using an MRI image of a person's head on the basis of machine learning, and thus multiphase collateral images may be rapidly generated.

The image generation method and the learning method according to an embodiment of the present disclosure may be performed in a computing device including a processor. According to an embodiment, the image generation method and the learning method may be separately performed in an image generation device and a learning device. Of course, the image generation method and the learning method may be performed in the same computing device, or the multiphase collateral image generation method may be performed in MRI equipment.

Hereinafter, embodiments of the present disclosure will be described in detail with reference to the accompanying drawings.

FIG. 1 is a block diagram of a learning device for generating multiphase collateral images according to an embodiment of the present disclosure.

Referring to FIG. 1, the learning device according to the present disclosure includes a data receiving unit 110, a brain mask generation unit 120, a preprocessing unit 130, and an image learning unit 140.

The data receiving unit 110 receives an MRI image of a head and multiphase collateral images generated on the basis of the MRI image, and the received MRI image and the multiphase collateral images for the received MRI image are training data for learning. MRI images for learning include MRI images of normal people as well as patients with cerebrovascular diseases.

The MRI image may be provided by MRI equipment. As an example, the MRI image may be a dynamic susceptibility contrast-magnetic resonance perfusion (DSC-MRP) image or a four-dimensional (4D)-magnetic resonance angiography (MRA) image. The multiphase collateral images for learning may be generated by an expert such as a clinical specialist.

The brain mask generation unit 120 generates a brain mask using the received MRI image. The MRI image of the head is an image of various types of tissue constituting the head such as a brain, a skull, and a cerebrospinal fluid. Since diagnosis of a cerebrovascular disease does not require an MRI image of tissue other than the brain, a brain mask is generated to extract an image of the brain from the MRI image.

The preprocessing unit 130 generates an MRI image and multiphase collateral images which are masked by the brain mask. The masked MRI image and the masked multiphase collateral images are images obtained by filtering out parts of the received MRI image and multiphase collateral images other than a cerebral region.

The image learning unit 140 learns the masked multiphase collateral images for the masked MRI image using a learning network.

Figure 2:
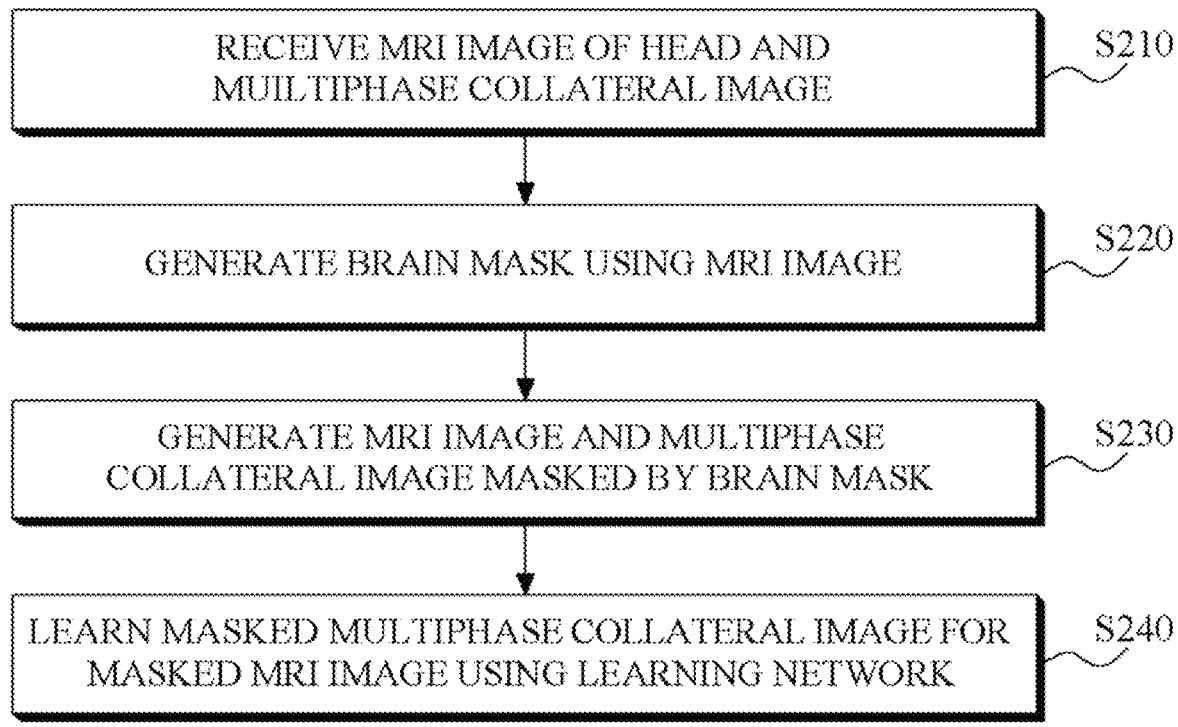
FIG. 2 is a diagram illustrating a learning method for generating multiphase collateral images according to an embodiment of the present disclosure.
Figure 3:
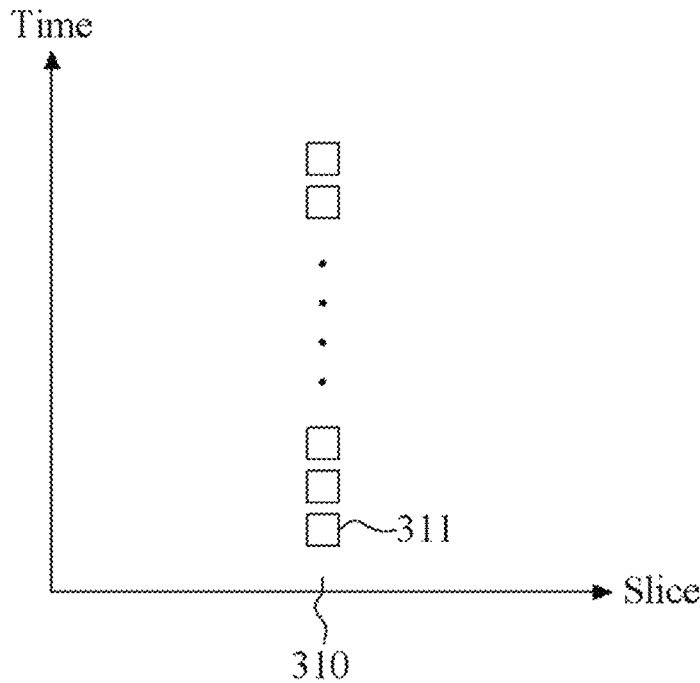
FIG. 3 is a diagram illustrating a four-dimensional (4D)-magnetic resonance angiography (MRA) image.

FIG. 2 is a diagram illustrating a learning method for generating multiphase collateral images according to an embodiment of the present disclosure, and FIG. 3 is a diagram illustrating a 4D-MRA image. In FIG. 2, a learning method performed in the learning device of FIG. 1 is illustrated as an embodiment.

The learning device according to the embodiment of the present disclosure receives an MRI image of a head and multiphase collateral images generated on the basis of the MRI image (S210) and generates a brain mask using the received MRI image (S220). The MRI image and the multiphase collateral images are training data. Then, the learning device generates an MRI image and multiphase collateral images masked by the brain mask (S230) and learns the masked multiphase collateral images for the masked MRI image using a learning network (S240).

The MRI image used in FIG. 2 includes a plurality of MRI images generated at a preset position in the head over time and are 4D images. DSC-MRP images or 4D-MRA images include a plurality of images generated according to preset positions (slices) of the head, that is, the brain, over time.

Referring to FIG. 3, for example, when the number of images captured at a specific slice 310 of the brain over time is 60 including a first image 311, five multiphase collateral images may be generated from the 60 images. Then, the learning device learns the five masked multiphase collateral images for 60 masked MRI images. The 60 masked MRI images become input images for the learning network, and the five masked multiphase collateral images are given as labels for the learning network.

Another learning network according to the embodiment of the present disclosure is a three-dimensional (3D) deep regression neural network and includes an encoding layer which generates a feature map for a masked MRI image through convolution and a decoding layer which increases a size of the feature map through deconvolution. The encoding layer serves to extract a feature value of a masked MRI image in a learning process, and the decoding layer serves to generate multiphase collateral images in an image generation process, that is, a process of estimating multiphase collateral images, to be described below.

According to the relationship between an input image for the learning network and a label, a weight of a filter used for convolution and deconvolution may be learned. Accordingly, multiphase collateral images for a target image input to the learning network may be estimated.

Meanwhile, although the embodiment of using a brain mask is illustrated in FIG. 2, learning may be performed without using a brain mask according to an embodiment. In other words, in operation S240, the learning device may learn multiphase collateral images input for an input MRI image using the learning network.

Figure 4:
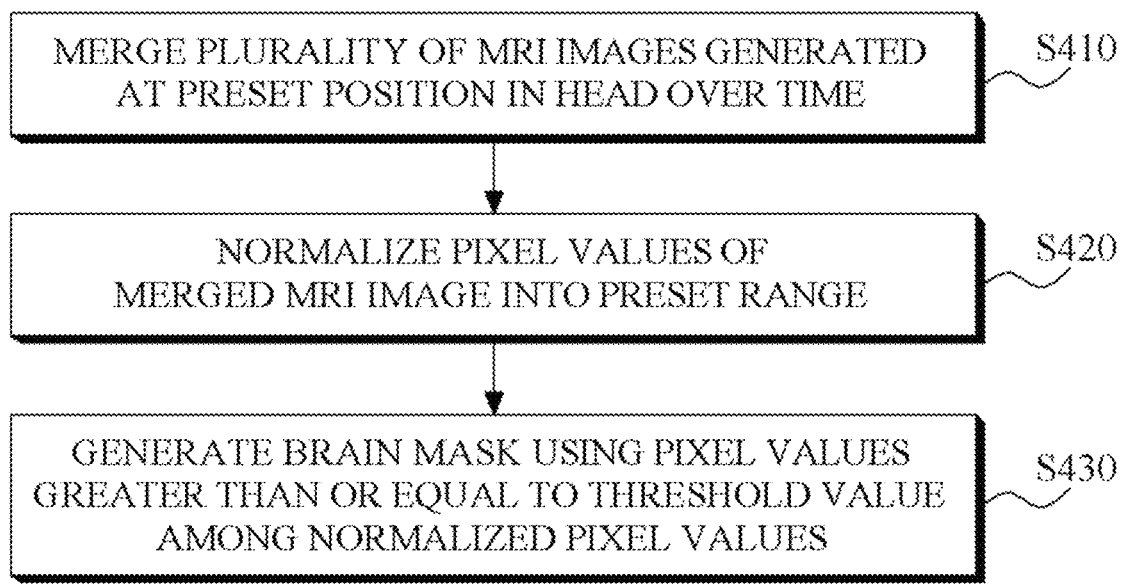
FIG. 4 is a diagram illustrating a method of generating a brain mask according to an embodiment of the present disclosure.
Figure 5A:
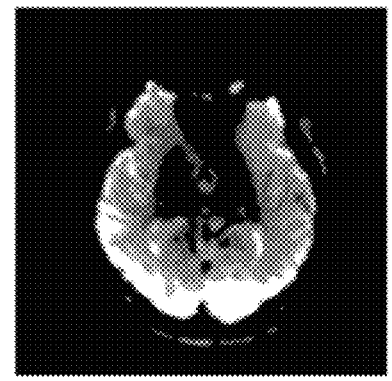
FIG. 5A, FIG. 5B, and FIG. 5C are a set of diagrams of a magnetic resonance imaging (MRI) image and a brain mask.
Figure 5B:
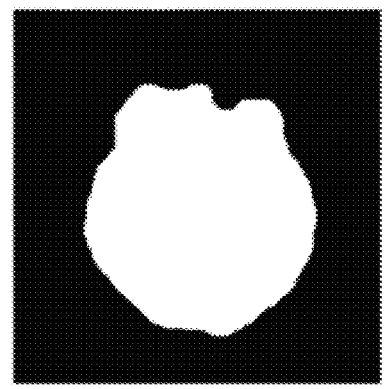
Figure 5C:
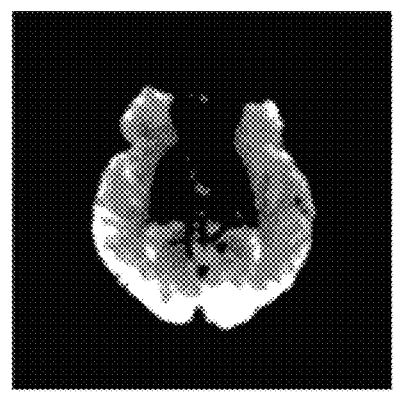

FIG. 4 is a diagram illustrating a method of generating a brain mask according to an embodiment of the present disclosure, and FIG. 5A, FIG. 5B, and FIG. 5C are a set of diagrams of an MRI image and a brain mask.

The learning device according to the embodiment of the present disclosure merges a plurality of MRI images which are generated over time at a preset position in a head (S410). For example, when 60 MRI images are generated as shown in FIG. 3, the learning device merges all the 60 MRI images. Here, merging means adding pixel values of pixels at the same position in different MRI images.

Then, the added pixel values of the merged MRI image is normalized into a preset range (S420). As an example, the learning device may normalize pixel values into a range from 0 to 1.

Subsequently, the learning device generates a brain mask using pixel values which are greater than or equal to a threshold value among the normalized pixel values (S430). The brain mask has the same size of the MRI image and extracts a region in which pixel values greater than or equal to the threshold value among normalized pixel values are present as a brain region from the MRI images.

Meanwhile, in a process of acquiring pixel values greater than or equal to the threshold value, the shape of the brain mask may be different from the shape of an actual brain due to an artifact and the like. Accordingly, the learning device may generate a brain mask through various morphological operations such as closing, erosion, and dilation.

FIG. 5B shows a brain mask for an MRI image shown in FIG. 5A, and FIG. 5C shows a masked MRI image. It may be seen that the image of FIG. 5C only includes a brain portion compared to the MRI image of FIG. 5A.

According to the embodiment of the present disclosure, only MRI images of brains are learned using a brain mask, and thus a learning rate can be increased.

Figure 6:
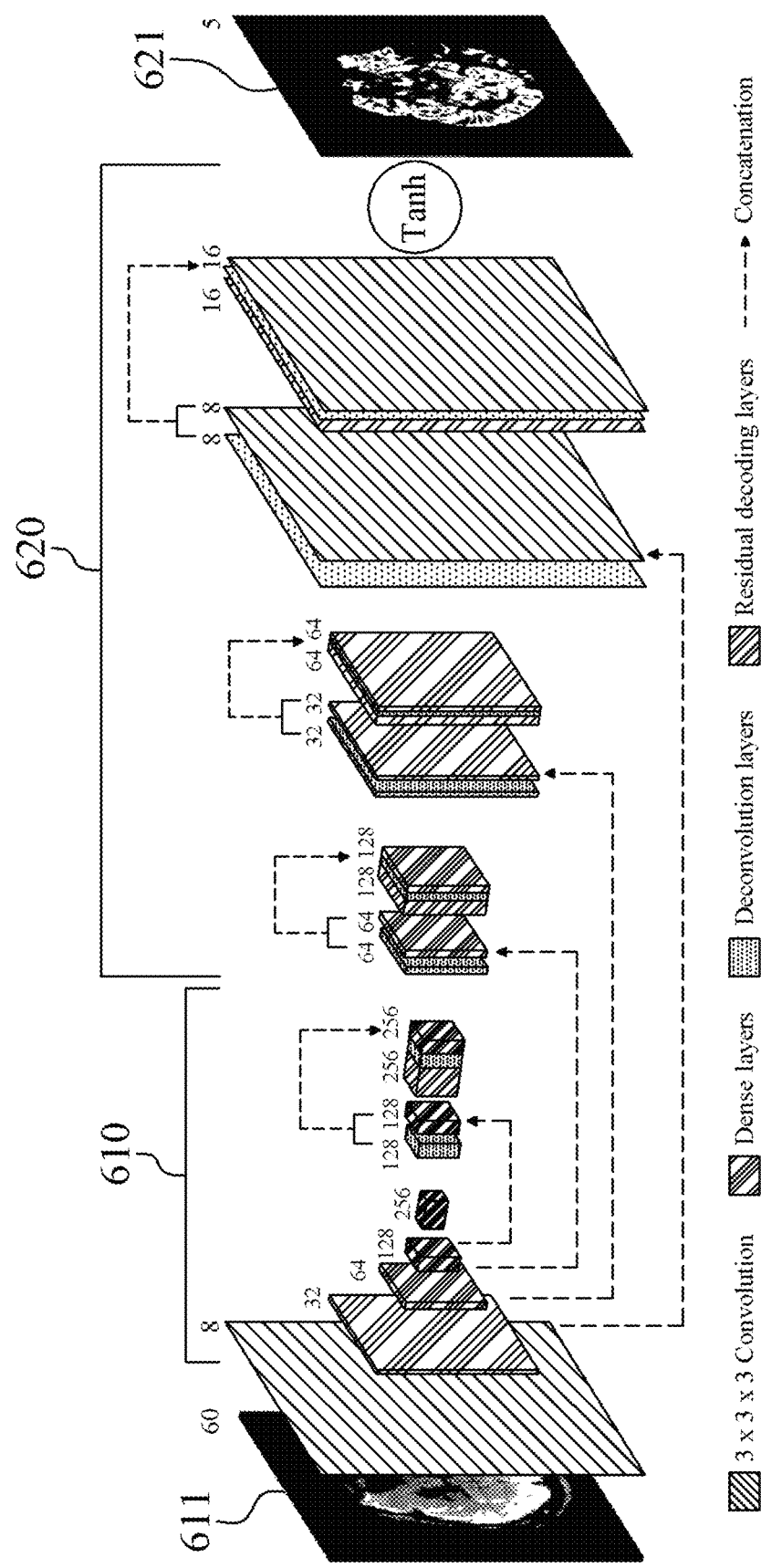
FIG. 6 is a block diagram of a learning network according to an embodiment of the present disclosure.

FIG. 6 is a block diagram of a learning network according to an embodiment of the present disclosure. In FIG. 6, a network which learns five multiphase collateral images 621 for 60 MRI images 611 is shown as an example.

An encoding layer 610 generates a feature map by performing convolution on the 60 MRI images 611 which are input images. The encoding layer 610 may have a densely connected convolutional networks (DenseNet) structure in which one layer is connected to all subsequent layers to promote reuse of feature information and smooth flow of feature information and gradients.

A decoding layer 620 increases a size of the feature map as much as the input images through deconvolution. Multiphase collateral images corresponding to the size of training data may be estimated through the decoding layer 620.

The size of a filter used for convolution and deconvolution or the detailed configuration of each layer may vary depending on embodiments, and an activation function other than the hyperbolic tangent function (Tanh) may be used.

The learning device according to the embodiment of the present disclosure may use ADAM among optimization algorithms used for machine learning and may perform efficient learning even with a small batch size using group normalization which has been recently disclosed by Yuxin Wu and Kaiming He.

Meanwhile, to increase learning efficiency, the learning device according to the embodiment of the present disclosure may adjust a weight of a filter used for learning according to the frequency of each pixel value of multiphase collateral images and learn masked multiphase collateral images. According to an embodiment, the learning device may calculate the frequency of each pixel value for all of the five multiphase collateral images and then perform learning or may calculate the frequency of each pixel value for each of the five multiphase collateral images and then perform learning.

Multiphase collateral images given as labels may be images whose pixel values are normalized into a certain range, for example, from −0.9 to 0.9. When pixel values of pixels of the multiphase collateral images are concentrated on a specific pixel value, that is, when there are a relatively large number of specific pixel values among the pixel values of the pixels, a weight for the specific pixel value increases, and learning efficiency may be degraded. Accordingly, the learning device according to the embodiment of the present disclosure may generate a weight vector according to a distribution pattern of pixel values of multiphase collateral images and perform regularization such that learning efficiency can be increased. As a normalization method, L2 normalization or L1 normalization used for machine learning may be used.

To generate a weight vector, the learning device generates a histogram by classifying the pixel values of the multiphase collateral images into a preset number of bins and normalizes the histogram into a preset range. The bins of the histogram correspond to specific pixel values and include frequency information of the specific pixel values of the multiphase collateral images. The learning device may calculate a logarithm of the inverse number of a frequency of a pixel value corresponding to each bin using the histogram and generate a weight vector for the pixel value of the multiphase collateral images.

Since a weight vector is generated using the inverse number of a frequency, it is possible to prevent a weight for a pixel value with a high frequency from being increased by normalization, and learning efficiency can be increased.

Figure 7A:
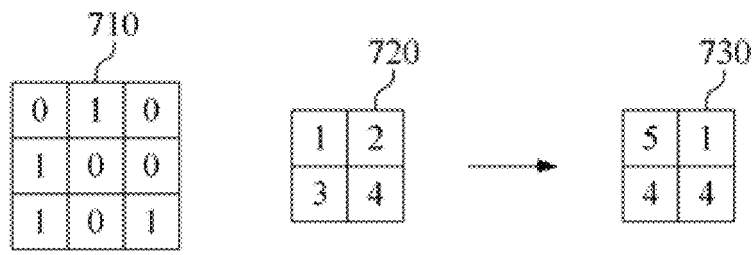
FIG. 7A and FIG. 7B are a diagram illustrating convolution and deconvolution.
Figure 7B:
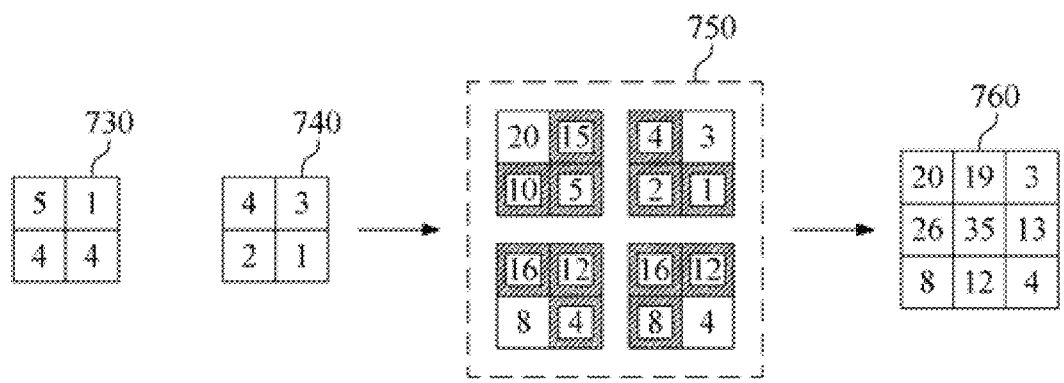

FIG. 7A and FIG. 7B are a diagram illustrating convolution and deconvolution.

Referring to FIG. 7A and FIG. 7B, FIG. 7A is a diagram illustrating a process of generating a feature map through convolution, and FIG. 7B is a diagram illustrating a process of increasing a size of the feature map through deconvolution.

In FIG. 7A, an input image 710 for the learning network has a size of 3×3, and a filter 720 used for convolution has a size of 2×2. Numbers written in the input image 710 indicate pixel values, and numbers written in the filter 720 indicate weights. The filter 720 moves up, down, left, and right with respect to the reference image 710, and pixel values and weights are multiplied and then added together such that a feature map 730 is generated.

In FIG. 7B, a filter 740 used for deconvolution has a size of 2×2. Each feature value of the feature map 730 generated through convolution is multiplied by four weights of the filter 740 such that one feature value is expanded to four feature values 750. For example, the feature value "5" of the feature map 730 is multiplied by each of the weights "4," "3," "2," and "1" of the filter and expanded to "20," "15," "10," and "5." Feature values expanded in this way are added such that a feature map 760 having a size of 3×3 is generated. In the block 750 showing the expanded feature values, hatched parts represent blocks which overlap each other and are added. For example, in the feature map 760 generated through deconvolution, the center feature value "35" is obtained by adding "5," "2," "12," and "16" in the block 750 representing the expanded feature values. According to an embodiment, deconvolution may be performed in various ways, such as padding, other than that described above.

Figure 8:
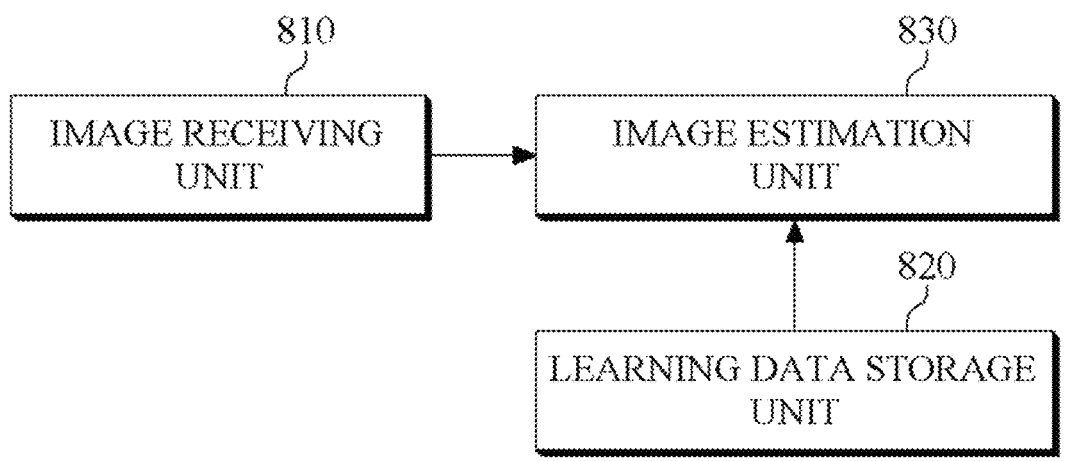
FIG. 8 is a diagram illustrating a device for generating multiphase collateral images using machine learning according to an embodiment of the present disclosure.

FIG. 8 is a diagram illustrating a device for generating multiphase collateral images using machine learning according to an embodiment of the present disclosure.

The device for generating multiphase collateral images according to the embodiment of the present disclosure includes an image receiving unit 810, a learning data storage unit 820, and an image estimation unit 830.

The image receiving unit 810 receives an MRI image of a subject's head, and such an MRI image may be provided by MRI equipment.

The learning data storage unit 820 stores learning data obtained through machine learning and may be, as an example, an artificial neural network such as a learning network. As described with reference to FIG. 2, the learning network is a network which has learned reference multiphase collateral images for reference MRI images. Here, reference represents training data used for learning.

The image estimation unit 830 generates multiphase collateral images for the received MRI image using the learning network stored in the learning data storage unit 820.

Figure 9:
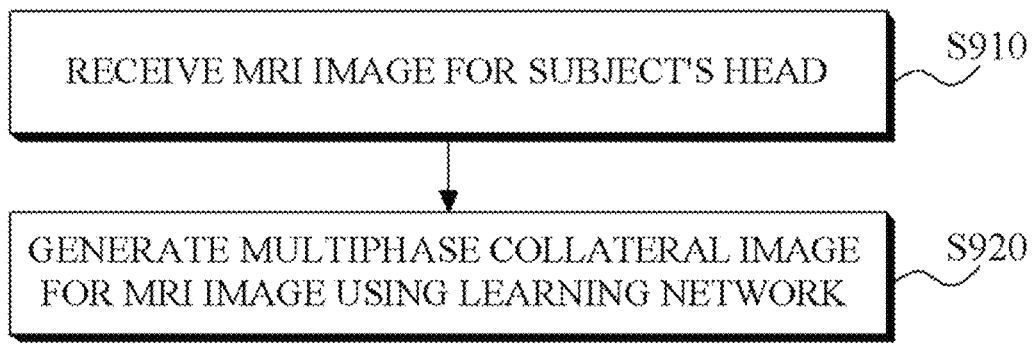
FIG. 9 is a diagram illustrating a method of generating multiphase collateral images using machine learning according to an embodiment of the present disclosure.

FIG. 9 is a diagram illustrating a method of generating multiphase collateral images using machine learning according to an embodiment of the present disclosure.

The device for generating multiphase collateral images using machine learning according to the embodiment of the present disclosure receives an MRI image of a subject's head (S910) and generates multiphase collateral images for the received MRI image using a learning network (S920).

The learning network includes an encoding layer which generates a feature map for a received MRI image through convolution and a decoding layer which generates multiphase collateral images by increasing a size of the feature map through deconvolution.

Meanwhile, according to embodiments, the device for generating multiphase collateral images according to the embodiment of the present disclosure may generate a brain mask for the subject using the received MRI image and apply the brain mask to the multiphase collateral images generated in operation S920. The brain mask may be generated as described with reference to FIG. 4.

According to the embodiment of the present disclosure, multiphase collateral images are estimated through machine learning. Accordingly, it is possible to rapidly generate multiphase collateral images, and a diagnosis rate of cerebrovascular diseases, such as stroke, can also be increased.

Also, according to the embodiment of the present disclosure, multiphase collateral images are generated without subjective judgment which may vary depending on experts. Accordingly, generation of multiphase collateral images and diagnosis of a cerebrovascular disease can be objectively performed.

The above-described technical content can be implemented in the form of program commands which may be executed by various computing means and recorded in a computer-readable medium. The computer-readable medium may include program commands, data files, data structures, etc. alone or in combination. The program commands recorded in the medium may be those specially designed or configured for the embodiments or those known to and available by those skilled in the computer software field. Examples of the computer-readable recording medium may include magnetic media, such as a hard disk, a floppy disk, or magnetic tape, optical media, such as a compact disc (CD) read-only memory (ROM) or a digital versatile disc (DVD), magneto-optical media, such as a floptical disk, and hardware devices configured to store and execute program commands such as a ROM, a random access memory (RAM), and a flash memory. Examples of the program commands may include high-level language code which can be executed by a computer using an interpreter and the like as well as machine language code generated by a compiler. The hardware devices may be configured to operate as one or more software modules to perform operations of the embodiments, and vice versa.

Although the present disclosure has been described above in conjunction with specific details, such as detailed elements, limited embodiments, and drawings, these are merely provided to aid in the overall understanding of the present disclosure, and the present disclosure is not limited to the embodiments. Rather, those skilled in the technical field to which the present disclosure pertains can make various modifications and alterations from the descriptions. Therefore, the spirit of the present disclosure should not be determined on the basis of the described embodiments, and the following claims, all equivalents to the claims, and equivalent modifications should be construed as falling within the scope of the spirit of the present disclosure.

What is claimed is:

1. A learning method for generating multiphase collateral images, the learning method comprising:
   receiving a magnetic resonance imaging (MRI) image of a head and multiphase collateral images generated on the basis of the MRI image;
   generating a brain mask using the MRI image;
   generating an MRI image and multiphase collateral images which are masked by the brain mask; and
   learning the masked multiphase collateral images for the masked MRI image using a learning network.

2. The learning method of claim 1, wherein the generating of the brain mask comprises:
   merging a plurality of MRI images generated at a preset position in the head over time;

normalizing pixel values of the merged MRI images into a preset range; and generating the brain mask using pixel values which are greater than or equal to a threshold value among the normalized pixel values.

3. The learning method of claim 1, wherein the learning of the masked multiphase collateral images comprises adjusting weights of a filter used for learning according to pixel-specific frequencies of the multiphase collateral images and learning the masked multiphase collateral images.

4. The learning method of claim 1, wherein the MRI image corresponds to a plurality of MRI images generated at a preset position in the head over time.

5. The learning method of claim 1, wherein the MRI image is a dynamic susceptibility contrast-magnetic resonance perfusion (DSC-MRP) image or a four-dimensional (4D)-magnetic resonance angiography (MRA) image.

6. A method of generating multiphase collateral images using machine learning, the method comprising:

receiving a magnetic resonance imaging (MRI) image of a subject's head;

and generating multiphase collateral images for the MRI image using a learning network, wherein the learning network is a network which has learned reference multiphase collateral images for reference IRI images;

wherein the learning network comprises:

an encoding layer configured to generate a feature map for the MRI image through convolution;

and a decoding layer configured to generate the multiphase collateral images by increasing a size of the feature map through deconvolution.

7. The method of claim 6, further comprising:

generating a brain mask for the subject using the MRI image; and applying the brain mask to the multiphase collateral images.

8. The method of claim 6, wherein the MRI image is a dynamic susceptibility contrast-magnetic resonance perfusion (DSC-MRP) image or a four-dimensional (4D)-magnetic resonance angiography (MRA) image.

* * * * *